United States Patent [19]
Salazar

[11] Patent Number: 6,008,222
[45] Date of Patent: Dec. 28, 1999

[54] METHOD FOR ORAL ADMINISTRATION OF BUSPIRONE AND NEFAZODONE

[75] Inventor: Daniel E. Salazar, Lawrenceville, N.J.

[73] Assignee: Bristol-Myers Squibb Company, Princeton, N.J.

[21] Appl. No.: 08/964,370

[22] Filed: Nov. 6, 1997

Related U.S. Application Data

[60] Provisional application No. 60/032,337, Dec. 4, 1996.

[51] Int. Cl.$^6$ .......................... A61K 31/40; A61K 31/495
[52] U.S. Cl. ............................. 514/255; 514/383
[58] Field of Search ............................ 424/400; 514/255, 514/383

[56] References Cited

U.S. PATENT DOCUMENTS

| | | |
|---|---|---|
| 3,717,634 | 2/1973 | Wu et al. . |
| 5,116,852 | 5/1992 | Gammans ................................ 514/359 |
| 5,431,922 | 7/1995 | Nicklasson . |
| 5,504,086 | 4/1996 | Ellinwood, Jr. et al. ............... 514/252 |
| 5,691,324 | 11/1997 | Sandyk .................................... 514/159 |
| 5,854,248 | 12/1998 | Marcus et al. .......................... 514/255 |

FOREIGN PATENT DOCUMENTS

WO 95/20980 of 0000 WIPO .

OTHER PUBLICATIONS

Mayol, et al., *Clin. Pharmacol. Ther.*, 37, 210, 1985.
Gammans, et al., *American J. Med.*, 80, Suppl. 3B, 41–51, 1986.
L. Krowczynski, *Extended Release Dosage Forms*, CRC–Press Inc., USA, 1987, ISBN 0–8493–4307–0.
Letters to editor in *J. Clin. Psychiatry*, 57, 7, Jul. 1996.
B. Cusack et al PsychoPharmacology (1994) 114: 559–565.
K. B. Weiss Drug and Aging 9(3) Sep. 9, 1996 191–201.

*Primary Examiner*—Peter F. Kulkosky
*Attorney, Agent, or Firm*—Richard P. Ryan

[57] ABSTRACT

An improved method for orally administering buspirone to a human subject wherein the bioavailability of buspirone is increased and its elimination, metabolite formation, and variability of these pharmacokinetic parameters is decreased, the improvement comprises the concurrent administration of a sufficient amount of nefazodone to effect these pharmacokinetic changes for orally administered buspirone.

8 Claims, No Drawings

METHOD FOR ORAL ADMINISTRATION OF BUSPIRONE AND NEFAZODONE

CROSS REFERENCE TO RELATED APPLICATION

This non-provisional application claims the benefit of U.S. provisional application 60/032,337 filed Dec. 4, 1996.

FIELD OF THE INVENTION

The present invention relates to an improved method for orally administering buspirone to a human subject. Co-administration of the drug nefazodone results in a higher ratio of buspirone, compared with its metabolite, into the general circulation. The rate of buspirone elimination and excessive variability in human pharmacokinetic parameters between dosing intervals is also reduced.

BACKGROUND OF THE INVENTION

Buspirone, chemically: 8-[4-[4-(2-pyrimidinyl)1-piperazinyl]butyl]-8-azaspiro(4,5)-decane,7,9-dione, is disclosed in U.S. Pat. No. 3,717,634 as a pharmaceutically active compound which has been found to be effective for the treatment of anxiety disorders and depression. However, buspirone shows a very high first pass metabolism and only about 4% of the administered dose will reach the systemic circulation unchanged after oral administration (Mayol et al., *Clin. Pharmacol. Ther.*, 37, 210, 1985). Great interindividual variations in buspirone absorption have also been observed as demonstrated by variations of the maximum plasma concentration of drug by up to ten-fold (Gammans et al., *American J. Med.*, 80, Suppl. 3B, 41–51, 1986). Metabolites have been identified, including several hydroxylated derivatives of buspirone that show low levels of pharmacological activity. The major metabolite, 1-(2-pyrimidinyl)-piperazine, (1-PP), has been found to demonstrate pharmacological activity in certain tests that suggest 1-PP itself possesses weak anxiolytic activity. However, in other tests 1-PP has shown that it antagonizes the desired anxiolytic and/or antidepressant action of buspirone.

The biological half-life of buspirone is very short and variable in man, on an order of 2–11 hours, whereas the major metabolite, 1-PP, has much slower elimination (Mayol et al., *Clin. Pharmacol. Ther.*, 37, 210, 1985). These pharmacokinetic properties necessitate a daily dosing regimen requiring repeat administration which would be expected to have a negative effect on patient compliance. Since buspirone is rapidly absorbed after an oral dose, peak plasma values of unchanged drug occur shortly after drug administration. As buspirone blood levels decline, blood levels of 1-PP increase, giving much higher plasma levels of 1-PP. These high levels of 1-PP have been associated with the occurrence of undesired or adverse events observed during the first days of treatment. Such adverse effects can also seriously impact patient compliance due to resultant deliberate disruption of the drug therapy. Since its clinical introduction, buspirone has suffered from a perceived lack of rapid onset which may be attributable in part to patient compliance and/or variable metabolism.

The physicochemical, pharmacokinetic and pharmacological properties of drugs and their formulations often dictate how a drug should be used in a therapeutic situation. A drug characterized by a short biological half-life should usually be administered in short dosing intervals to maintain the plasma concentration levels that provide the pharmacologic action. As mentioned above, this often reduces patient compliance and as a result leads to underdosing between the dosage intervals. An ideal oral dosage form would be a once-daily formulation able to maintain the therapeutic drug levels in the body for 24 hours, yet without the risk of any adverse reactions.

Among formulations devised to avoid limitations due to a short biological half-life (rapid metabolism/elimination) have been various dosage forms which provide release of the desired drug over an extended period of time, thereby slowing the drug's absorption. Over the past two decades considerable progress has been made in developing controlled/extended release technologies for drug compounds. The design of various controlled/extended release formulations and their technologies are known in the art (L. Krowczynski, Extended Release Dosage Forms, CRC-Press Inc., USA, 1987, ISBN 0-8493-4307-0).

Some important advantages of such delivery systems can be:

reduction of the frequency of dosing (with a concomitant increase in patient compliance);

maintenance of therapeutic plasma drug levels for a longer period of time than would be indicated by the drug's biological half-life;

reduction of undesired adverse reactions/toxicity (by suppression of the initial high plasma concentration peaks of drug/metabolite); and, in some instances, reduction of the amount of drug required for treatment (by reduction of the initial high concentration spike and rapid elimination of drug).

In order to capture these advantages, controlled/extended release formulations of buspirone and its salts were developed and disclosed in U.S. Pat. No. 5,431,922. Although the initial objectives for these buspirone extended release formulations were realized; e.g. an improved pharmacokinetic profile for buspirone blood levels, reduction of 1-PP peak blood levels, and increased time intervals between dosing; a high level of variability in the pharmacokinetic parameters, particularly with buspirone and 1-PP blood levels over time, between dosing periods and between patients became problematic. To this point in time, the formulations that were the subject of U.S. Pat. No. 5,431,922 have not been commercialized.

Recently, a method for increasing bioavailability of orally administered hydrophobic pharmaceutical compounds was disclosed in WO 95/20980. The method comprises concurrent administration of a compound that inhibits cytochrome P4503A enzymes or P-glycoprotein-mediated membrane transport. While lists of compounds that can be substrates and compounds that can act as inhibitors were disclosed, neither buspirone nor nefazodone was mentioned. The only inhibitor exemplified was ketoconazole.

Nefazodone has been disclosed as being an inhibitor of cytochrome P4503A4. Recently a letter to the editor in *J. Clin. Psychiatry*, 57:7, July 1996, referred to nefazodone's reported inhibition of cytochrome P4503A3/4 and its related effect of increasing the concentration and toxicity of alprazolam and triazolam. Further study was recommended in order to determine whether this inhibitory effect on cytochrome by nefazodone might represent a therapeutic asset by increasing/stabilizing plasma concentrations of certain CYP3A3/4 substrates.

Other reports of a differing drug interaction effect have appeared over the past few years. These reports suggest that several agents, one being buspirone, have been effective in augmentation of an antidepressant effect when co-administered with an antidepressant drug regimen such as fluoxetine. A pharmacokinetic study of the co-administration of nefazodone with buspirone was undertaken as a preliminary step to clinically study augmenting effect on the antidepressant drug nefazodone. An striking result was observed: concurrent administration of nefazodone with buspirone demonstrated that nefazodone had a marked effect on buspirone and 1-PP pharmacokinetics.

Nothing in the previous references or prior art has disclosed or suggested the advantageous improvements in oral buspirone's pharmacokinetics and metabolism resulting from concomitant administration of the antidepressant drug nefazodone.

SUMMARY OF THE INVENTION

The invention concerns an improved method for oral administration of the useful drug buspirone. The method comprises concurrent administration of the antidepressant agent nefazodone which results in an increase in buspirone plasma concentrations with a concomitant decrease in plasma concentrations of its major metabolite 1-pyrimidin-2-ylpiperazine (1-PP). Additionally, the disappearance of buspirone is delayed and intra- and inter-patient variations in buspirone and 1-PP blood levels are reduced. The present invention also comprises compositions and pharmaceutical kits containing nefazodone and buspirone for combination therapy. The combination of nefazodone with buspirone for oral administration is expected to provide a more efficient and effective use of buspirone for treatment of anxiety, depression, substance addiction, and other disorders for which buspirone has demonstrated clinical utility.

DETAILED DESCRIPTION OF THE INVENTION

Buspirone undergoes extensive first pass metabolism with a ten-fold variation between subjects. Previous attempts to improve these aspects of orally administered buspirone by pharmaceutical formulations, e.g. controlled release, have not been completely successful. Also, the large plasma concentrations of the major metabolite, 1-PP, are believed to interfere with the anxiolytic and/or antidepressant effect of buspirone itself. It has long been an objective to develop an oral dosing formulation of buspirone that exhibited decreased metabolism and elimination as well as minimizing the large variations in pharmakinetic parameters observed between subjects dosed orally with buspirone.

In the course of early clinical studies designed to investigate potential augmentation of the response seen with antidepressant agents, buspirone (the potential AD enhancer) and nefazodone (the AD agent) were administered concurrently. Examination of the pharmacokinetic parameters of buspirone indicated that, unexpectedly, concomitant administration of antidepressant doses of nefazodone with 5 mg buspirone increases buspirone C max (maximum plasma concentration) and AUC (area under the curve) values by about 13-fold and 21-fold, respectively. For the major metabolite 1-PP, C max decreased by about 60% and AUC values by about 50%.

The invention resulting from this discovery achieves the objectives of previous extended release formulations while overcoming the intra- and inter-patient variability in buspirone pharmacokinetic parameters seen with these ER formulations. In effect, the oral dosing method of the present invention provides:

increased plasma concentrations of unchanged drug buspirone per unit dosed;

reduced plasma levels of the objectionable metabolite, 1-PP per unit buspirone dosed;

decreased rate of elimination of buspirone from the patient's plasma and a concomitant increase in drug exposure;

decreased variability in buspirone plasma concentrations and in rate of elimination.

These effects result in several advantages for patients when administered buspirone orally. The increased ratio of buspirone to 1-PP plasma concentrations should strengthen efficacy of treatment. Pharmacologic studies have shown that 1-PP can antagonize beneficial effects of buspirone with respect to treating anxiety and depression. Reduction of 1-PP levels is also believed to correlate with a reduced incidence and severity of unwanted side-effects; whereas the increased bioavailability of unchanged drug should avoid underdosing between dosing intervals. The prolonged buspirone plasma concentrations should also allow for less frequent dosing which, when combined with increased drug tolerability, should increase patient compliance. Simply put, the concurrent administration of nefazodone can assure effective levels of buspirone are achieved and prolong the duration of buspirone's effect so that less frequent administration would be required. As the variability within and between patients in plasma concentrations is reduced, therapeutic response should be more consistent. Clinical observations indicate good patient tolerability of the buspirone-nefazodone combination and this further benefits the utility of the method of this invention.

The present invention also provides a more efficient and effective method for treatment of various clinical disorders in which buspirone can be utilized. Buspirone has been disclosed as having therapeutic utility in treating such disorders as anxiety, depression, mixed anxiety and depression, substance addiction, alcohol abuse, panic disorders, sexual dysfunction, sleep apnea, eating disorders, and attention deficit disorder. As one aspect of the invention, the method comprises concurrent oral administration to a subject of a therapeutically effective amount of 1) buspirone and 2) nefazodone in an amount sufficient to favorably affect the pharmacokinetic parameters for the administered buspirone. The synergy of this combination is expected to greatly increase the efficacy and efficiency of buspirone treatment.

An increase in the buspirone to 1-PP ratio appears to be desirable from a therapeutic viewpoint. The results of pharmacologic studies indicate that the metabolite, 1-PP, can antagonize beneficial effects of buspirone. Social interaction paradigms that measure levels of anxiety have shown that 1-PP has an anxiogenic effect when administered to diazepam-withdrawn animals. Previous studies had not shown any effect of 1-PP on social interaction in diazepam-naive subjects. Azapirone anxiolytics, such as buspirone, have failed to adequately treat patients undergoing diazepam-withdrawal, a common condition in populations of anxious patients. These experiments produce evidence that increased anxiogenesis and loss of efficacy in this specific patient population can be attributed to 1-PP. This is an interesting effect in light of 1-PP's (weak) antianxiety activity observed in earlier animal testing.

In studies of depression, buspirone was tested systemically and intracerebrally in a rat forced-swim test which is a useful screening procedure for antidepressant agents. Buspirone was active when given intracerebrally, but inactive when given systemically (where large amounts of 1-PP result). The activity of intracerebral buspirone could be blocked by systemic administration of 1-PP, thereby demonstrating its antagonism of buspirone's antidepressant effect. On the basis of these and other studies, the present improved method of buspirone administration which reproducibly increases the ratio of unchanged buspirone to 1-PP would be expected to enhance the desired anxiolytic and antidepressant effects of buspirone. Thus, the improved method of the instant invention produces a non-obvious therapeutic advantage over previous methods of orally administering conventional formulations of buspirone.

In regard to single agent or combined agent formulations of buspirone and nefazodone to be employed in the improved method, considerable variation in formulations and components may be practiced without departing from the instant invention. Any salt form of buspirone and/or nefazodone having acceptable formulation properties can be used, for instance: acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, (embonate), pantothenate, phosphate/diphosphate, polygalacturonate, salicylate, stearate, subacetate, succinate, sulphate, tannate, tartrate, teoclate, triethiodide. Hydrates and other pharmaceutically acceptable solvates are also included. The hydrochloride salts of both nefazodone and buspirone are preferred however.

The present invention then comprises the concurrent administration of a therapeutically effective amount of buspirone and a buspirone pharmacokinetic-affecting amount of nefazodone to a patient having a disorder for which buspirone can be used in its treatment. Such a treatment provides a greater window of efficacy by increasing and prolonging the presence of buspirone in the patient's blood while reducing potential side effects of buspirone's major metabolite 1-PP by decreasing its levels in the patient's blood.

By "therapeutically effective amount" is meant an amount of buspirone or one of its salts than when administered alone or in combination formulation is effective to treat the various disorders for which buspirone has been disclosed as a useful treatment.

By "concurrent administration," "administered in combination," or the like, when referring to the nefazodone component and the buspirone component of the present method, it is meant that the components are administered concurrently to a mammal being treated. By concurrently, it is meant that each component may be administered at the same time or sequentially in any order at different points in time; however, if not administered at the same time, they should be administered sufficiently closely in time so as to provide the desired treatment effect. Suitable dosing intervals and dosing order with such compounds will be readily apparent to those skilled in the art, once armed with the present disclosure. Preferably, all components are administered at the same time, and if not administered at the same time, preferably they are all administered less than one hour apart from one another.

In a composition of the invention, nefazodone and buspirone are combined and given at various dose ratios based on the weight of buspirone deemed therapeutic for the targeted disorder and the weight of nefazodone sufficient to provide the desired enhancement of buspirone pharmacokinetics.

In general, buspirone would be administered at levels in accordance with guidelines found in standard medical/drug references such as the "Physicians Desk Reference" and the like. Generally, this would be in the range of 2.5 to 10 mg per dose for buspirone. Amounts of nefazodone for concurrent administration would generally be in the range of 50 to 500 mg and preferably about 100 to 200 mg.

The present invention also includes pharmaceutical compositions (that is, combination products), such pharmaceutical compositions (combination products) comprising or consisting essentially of, in combination, the buspirone component and the nefazodone component. Such compositions may be in solid or liquid dosage units and may further include a suitable pharmaceutical carrier.

The present invention also includes pharmaceutical kits comprising or consisting essentially of buspirone or one of its salts together with nefazodone or one of its salts. In the kit, the buspirone component and the nefazodone component may each be presented in separate vials as compounds, and/or in separate vials as compounds in combination with a pharmaceutically acceptable carrier. Alternatively, the buspirone component and the nefazodone component may be combined together in one or more vials, with or without a carrier. Thus, for example, the invention includes pharmaceutical kits comprising a separate vial comprising the buspirone component and a separate vial comprising the nefazodone component, each vial also containing, if desired, a carrier.

The compositions and kits of the present invention may be employed in the treatment of alcoholism and alcohol dependence; anxiety; anxiety with depression; depression; sleep apnea; eating disorders; substance addiction; sexual dysfunction; hostility; panic disorders; post-traumatic stress disorder; attention deficit disorder; as well as for improving short-term memory and post-myocardial infarction recovery as well as any other conditions and disorders for which buspirone has been found to be useful.

The preparation of both buspirone and nefazodone can be found in the literature. Specifically, buspirone, its preparation, and formulations are described in U.S. Pat. No. 3,717,634; nefazodone and its preparation and formulation in U.S. Pat. No. 4,338,317. Other synthetic processes for buspirone have been disclosed and buspirone itself is available commercially from bulk drug manufacturers. The buspirone and nefazodone U.S. patents are incorporated herein in their entirety.

Dosage and Formulation

The buspirone component and nefazodone component combination treatment of the invention can be administered orally by any conventional means available for the use in conjunction with pharmaceuticals, either as individual separate dosage units administered simultaneously or concurrently, or in a physical combination of each component therapeutic agent in a single or combined dosage unit. The active agents can be administered alone, but are generally administered with a pharmaceutical carrier selected on the basis of standard pharmaceutical practice.

The dosage administered will, of course, vary depending on the use and known factors such as the age, health, and weight of the recipient; nature and extent of symptoms, kind of concurrent treatment, frequency of treatment, and the effect desired. The recipient may be any type of mammal, but is preferably a human.

In the methods of the present invention, the two compounds, buspirone and nefazodone can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, and the like. Disintegrators include, without limitation, starch, methyl cellulose, agar, bentonite, xanthan gum, and the like.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

The proper dosage of the buspirone component and the nefazodone component in this invention will be readily ascertainable by a medical practitioner skilled in the art, based upon the present disclosure. By way of general guidance; typically, a daily dosage may be about 2.5 to 10 mg of buspirone and from about 50 to 500 mg of nefazodone.

The combination products of this invention may be formulated such that, although the active ingredients are combined in a single dosage unit, the physical contact between the active ingredients is minimized. In order to minimize contact, for example, one or more of the active ingredients may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention provides for a combination product wherein one or more of the active ingredients is coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one or more components is coated with a sustained and/or enteric release polymer, and the other(s) component is also coated with a polymar such as a low viscosity grade of hydroxypropyl methylcellulose or other appropriate materials as known in the art, in order to further separate the active components. The polymer coating serves to form an additional barrier to interaction with the other component.

Dosage forms of the combination products of the present invention wherein one active ingredient is enteric coated can be in the form of tablets such that the enteric coated component and the other active ingredients are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the present invention, whether administered in a single dosage form or administered in separate forms but at the same time or concurrently by the same manner, will be readily apparent to those skilled in the art, based on the present disclosure.

Pharmaceutical kits useful for the treatment of disorders and conditions listed hereinabove, which comprise a therapeutically effective amount of the buspirone component and the nefazodone component, in one or more containers, are also within the ambit of the present invention. Sterilization of the container may be carried out using conventional sterilization methodology well known to those skilled in the art. The buspirone component and the nefazodone component may be in the same container or in separate containers. The containers of materials may comprise separate containers, or one or more multi-part containers, as desired. The buspirone component and the nefazodone component may be separate or physically combined into a single dosage form or unit as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

Specific Embodiments

Results of a six subject pharmacokinetic study are tabulated below. Buspirone and 1-PP blood levels were ascertained for each subject following seven days of drug (buspirone=treatment A; buspirone+nefazodone=treatment B) administration. Dosages were 5 mg buspirone HCl (bid) for treatment A, and 5 mg buspirone and 250 mg nefazodone HCl (both given bid) for treatment B.

|  | Buspirone, ng/ml | | 1-PP, ng/mL | |
| --- | --- | --- | --- | --- |
| Parameter | Busp. Only | Busp. + Nefaz. | Busp. Only | Busp. + Nefaz. |
| Cmax (ng/mL) | 0.6 ± 0.7* | 8.0 ± 3.3 | 3.4 ± 2.2 | 1.4 ± 0.9 |
| Tmax (hr) | 1.0 (0.5, 1.5)** | 1.0 (0.5, 2.5) | 1.0 (1.0, 6.0) | 1.0 (0.5, 5.0) |
| T½ (hr) | 2.6 ± 1.8 | 3.6 ± 0.6 | 3.4 ± 1.0 | 7.7 ± 4.3 |
| AUC (0 – t) (ng · hr/mL) | 1.4 ± 1.6 | 29.4 ± 9.9 | 16.8 ± 9.9 | 8.9 ± 7.6 |

*Mean (±SD)
**Median (range)

These preliminary study data indicate that the concomitant administration of nefazodone with buspirone increases buspirone Cmax and AUC values by about 13-fold and 21-fold, respectively, with corresponding decreases observed in 1-PP (major buspirone metabolite) Cmax and AUC values by about 60% and 50%, respectively. Thus, the preliminary study data reflect a marked inhibition of buspirone metabolism in the presence of nefazodone.

Various modifications of the invention in addition to those shown and described herein will be apparent to those skilled in the art from the foregoing description. Such modifications are also intended to fall within the scope of the appended claims.

I claim:

1. An improved method for orally administering buspirone to a patient in need thereof comprising the concurrent administration of a therapeutically effective amount of buspirone, or a pharmaceutically acceptable salt thereof as component 1, with nefazodone, or a pharmaceutically acceptable salt thereof, as component 2, in an amount sufficient to provide a higher ratio of buspirone, compared with its metabolite, in the patient's bloodstream.

2. The method of claim 1 wherein buspirone HCl is component 1.

3. The method of claim 1 wherein nefazodone HCl is component 2.

4. The method of claim 2 wherein nefazodone HCl is component 2.

5. The method of claim 1 wherein components 1 and 2 are administered separately.

6. The method of claim 1 wherein components 1 and 2 are administered in combination.

7. A pharmaceutical composition comprising a therapeutically effective amount of buspirone, or a pharmaceutically acceptable salt thereof, as component 1 and nefazodone, or a pharmaceutically acceptable salt thereof as component 2, in an amount sufficient to favorably affect the pharmacokinetics of component 1.

8. A pharmaceutical composition of claim 6 wherein component 1 is buspirone HCl and component 2 is nefazodone HCl.

* * * * *